(12) United States Patent
Lange et al.

(10) Patent No.: US 7,799,060 B2
(45) Date of Patent: Sep. 21, 2010

(54) MULTI-DIRECTIONAL SPINAL STABILIZATION SYSTEMS AND METHODS

(75) Inventors: Eric C. Lange, Collierville, TN (US); Jonathan Dewey, Memphis, TN (US); Thomas Carls, Memphis, TN (US); Aurelien Bruneau, Memphis, TN (US); Kent M. Anderson, Memphis, TN (US); Fred J. Molz, IV, Collierville, TN (US); Matthew M. Morrison, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 937 days.

(21) Appl. No.: 11/156,375

(22) Filed: Jun. 20, 2005

(65) Prior Publication Data

US 2007/0005062 A1     Jan. 4, 2007

(51) Int. Cl.
*A61B 17/70*     (2006.01)
(52) U.S. Cl. ...................................... 606/257; 606/263
(58) Field of Classification Search ................... 606/61, 606/60, 246–264, 279
See application file for complete search history.

(56) References Cited

U.S. PATENT DOCUMENTS

| 4,917,700 | A | * | 4/1990 | Aikins | 623/13.19 |
|---|---|---|---|---|---|
| 5,030,220 | A | * | 7/1991 | Howland | 606/261 |
| 5,092,893 | A | * | 3/1992 | Smith | 606/61 |
| 5,352,224 | A | * | 10/1994 | Westermann | 606/286 |
| 6,248,106 | B1 | | 6/2001 | Ferree | |
| 6,423,065 | B2 | * | 7/2002 | Ferree | 606/61 |
| 6,514,255 | B1 | | 2/2003 | Ferree | |
| 6,582,433 | B2 | | 6/2003 | Yun | |
| 6,626,909 | B2 | | 9/2003 | Chin | |
| 6,730,092 | B2 | | 5/2004 | Songer | |
| 6,852,128 | B2 | * | 2/2005 | Lange | 623/17.11 |
| 6,989,011 | B2 | * | 1/2006 | Paul et al. | 606/61 |
| 7,220,262 | B1 | * | 5/2007 | Hynes | 606/279 |
| 2002/0120270 | A1 | * | 8/2002 | Trieu et al. | 606/61 |
| 2002/0133155 | A1 | * | 9/2002 | Ferree | 606/61 |
| 2003/0055427 | A1 | * | 3/2003 | Graf | 606/61 |
| 2004/0049190 | A1 | * | 3/2004 | Biedermann et al. | 606/61 |
| 2004/0260287 | A1 | * | 12/2004 | Ferree | 606/61 |
| 2005/0267470 | A1 | * | 12/2005 | McBride | 606/61 |
| 2006/0052786 | A1 | * | 3/2006 | Dant et al. | 606/61 |
| 2006/0217712 | A1 | * | 9/2006 | Mueller et al. | 606/61 |

FOREIGN PATENT DOCUMENTS

| DE | 32 19 575 A1 | 12/1983 |
|---|---|---|
| GB | 2 382 304 A | 5/2003 |

* cited by examiner

*Primary Examiner*—Eduardo C Robert
*Assistant Examiner*—Tara R Carter

(57) ABSTRACT

Systems and methods for multi-directional stabilization of a spinal column segment are provided. The systems include one or more motion preserving constructs that are engaged to adjacent vertebrae and extend trans-axially between the vertebrae obliquely to the central axis of the spinal column. The systems permit motion of at least a portion of a vertebral level while providing stabilization at least when tensioned. Systems that provide stabilization in compression are also contemplated.

19 Claims, 3 Drawing Sheets

MULTI-DIRECTIONAL SPINAL STABILIZATION SYSTEMS AND METHODS

BACKGROUND

Various types of devices and systems have been used to stabilize portions of bones including the spine. Spinal stabilization techniques have employed plating and rods on the posterior, anterior, lateral, postero-lateral and antero-lateral portions of a spinal column segment. Such systems can provide rigid or dynamic fixation of a spinal column segment for the repair of injured or diseased vertebrae, intervertebral discs, and other elements of the spinal column. There remains a need for stabilization systems that are adaptable for various stabilization requirements in a single spinal procedure.

SUMMARY

According to one aspect, a multi-directional spinal stabilization system is provided that includes a motion preserving construct extending trans-axially between pedicles of adjacent vertebrae.

According to another aspect, there is provided a multi-directional spinal stabilization system that includes a first anchor engageable to a first vertebra on a first side of a central axis of a spinal column and a second anchor engageable to the first vertebra on a second side of the central axis and a third anchor engageable to a second vertebra on the first side of the central axis and a fourth anchor engageable to the second vertebra on the second side of the central axis.

In one form, the system includes a first stabilization construct with an elongate flexible body in the form of a loop positionable about the first and fourth anchors. The system further includes a second stabilization construct with an elongate flexible body in the form of a loop positionable about the second and third anchors. When engaged to the respective anchors, the second stabilization construct extends transversely to the first stabilization construct and each of the first and second stabilization constructs are obliquely oriented to the central axis.

In another form, the system includes a stabilization construct with an elongate flexible body having a first trans-axial portion engageable to the first anchor and extendable obliquely across the central axis to the fourth anchor. The construct further includes a second trans-axial portion engageable to the second anchor and extendable obliquely across the central axis to the third anchor. The stabilization construct also includes a connecting portion extendable between the third and fourth anchors. The stabilization construct is slidable relative to the third and fourth anchors in response to axial rotation of the first and second vertebrae to maintain tension on the stabilization construct.

In a further form, the system includes a flexible, compressible stabilization construct including a central body positionable between the first, second, third and fourth anchors along the central axis. The stabilization construct further includes a first arm extending from the central body to the first anchor, a second arm extending from the central body to the second anchor, a third arm extending from the central body to the third anchor, and a fourth arm extending from the central body to the fourth anchor. The arms are each obliquely oriented to the central axis and the stabilization construct limits distraction and compression of the first and second vertebrae when engaged to the anchors.

According to another aspect, a multi-directional spinal stabilization system includes a first member structured for positioning between and engagement to said first and second anchors engaged bi-laterally or on opposite sides of the central axis of a first vertebra and a second member structured for positioning between and engagement to said third and fourth anchors engaged bi-laterally or on opposite sides of a central axis of a second vertebra. A third member is engageable to the first member between the first and second anchors. The third member is structured to extend from the first member to the second member. The third member is further engageable to the second member between the third and fourth anchors. At least one of said first, second and third members is flexible and at least one other of the first, second and third members is rigid.

In another aspect, methods for multi-directional spinal stabilization are provided. The method includes engaging a first anchor to a first vertebra on a first side of a central axis of the spinal column; engaging a second anchor to the first vertebra on a second side of the central axis; engaging a third anchor to a second vertebra on the first side of the central axis; and engaging a fourth anchor to the second vertebra on the second side of the central axis.

In one form, the method further includes positioning a first elongate stabilization construct about the first anchor and the fourth anchor in an oblique orientation to the central axis; and positioning a second elongate stabilization construct about the second anchor and the third anchor in an oblique orientation to the central axis, wherein the first and second stabilization constructs each form a loop extending between the respective anchors to which each is engaged.

In another form, the method further includes fixing a first end of an elongated, flexible stabilization construct to the first anchor; extending the stabilization construct from the first anchor trans-axially and obliquely to the central axis to the fourth anchor; securing the stabilization construct to the fourth anchor; extending stabilization construct trans-axially from the fourth anchor to the third anchor; securing the stabilization construct to the third anchor; extending the stabilization construct from the third anchor trans-axially to and obliquely to the central axis to the second anchor; and fixing a second end of the stabilization construct to the second anchor, wherein the stabilization construct is slidable relative to the third and fourth anchors in response to axial rotation of the spinal column segment.

These and other aspects are discussed further below.

DESCRIPTION OF THE ILLUSTRATED EMBODIMENTS

Figure 1:
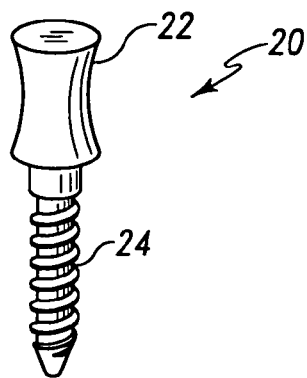
FIG. 1 is a view of one embodiment anchor engageable to a vertebral body.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and any such further applications of the principles of the invention as illustrated therein are contemplated as would normally occur to one skilled in the art to which the invention relates.

Multi-directional stabilization systems are provided for attachment to a spinal column segment. The systems include one or more stabilization constructs positionable along at least one level of the spinal column and engageable thereto to provide multi-directional stabilization. The stabilization constructs include motion preserving capabilities to allow motion of the motion segment while limiting extension, flexion and/or axial rotation of the motion segment to provide effective dynamic stabilization.

The systems can be engaged posteriorly, anteriorly, antero-laterally, laterally, or in any other position to the spinal column segment. Combinations of approaches and stabilization are also contemplated such as, for example, anterior and posterior stabilization systems. The systems can be employed with fusion of one or more vertebral levels with bone graft alone or in combination with one or more fusion devices in a disc space between vertebrae. Furthermore, the systems can be employed with artificial discs or motion preserving devices in one or more vertebral levels. The fusion devices and artificial discs can be positioned through the same approach or through differing approaches than that taken for placement of the stabilization systems.

In FIG. 1 there is shown one embodiment of an anchor 20 engageable to a vertebral body. Any of the stabilization systems discussed herein may include a number of anchors 20 engageable to vertebrae along the spinal column segment to couple construct 30 to one or more of the vertebra. Each of the anchors 20 can include a receiving portion 22 and an anchoring portion 24. Anchoring portion 24 may include any suitable form for engaging one or more of the vertebrae. Examples of contemplated forms for anchoring portion 24 include bone screws either multi-axial or uni-axial in form, hooks, staples, and interbody devices, for example. The anchoring portions for any two or more of the anchors may be of the same form or of different forms. Receiving portion 22 may be in the form of a post, saddle, clamp, top-loading connector, side-loading connector, bottom-loading connector, or any other suitable device for engaging construct 30 with the respective anchor portion 24. Receiving portions 22 may be of the same form for each of the anchors 20, or of differing forms.

In the illustrated embodiments of FIGS. 2-8, spinal column segment 10 extends along a central axis 11. Spinal column segment 10 includes an upper or superior vertebra 12 and a lower or inferior vertebra 14. Vertebrae 12, 14 comprise a spinal motion segment with a disc space 16 therebetween. Applications are also contemplated in which there are three or more vertebrae in the spinal column segment. Anchor 20a is engaged to vertebra 12 along one side of central axis 11, and anchor 20b is engaged to vertebra 12 on an opposite side of central axis 11. Similarly, anchor 20c is engaged to vertebra 14 along one side of central axis 11, and anchor 20d is engaged to vertebra 14 on an opposite side of central axis 11.

Figure 2:
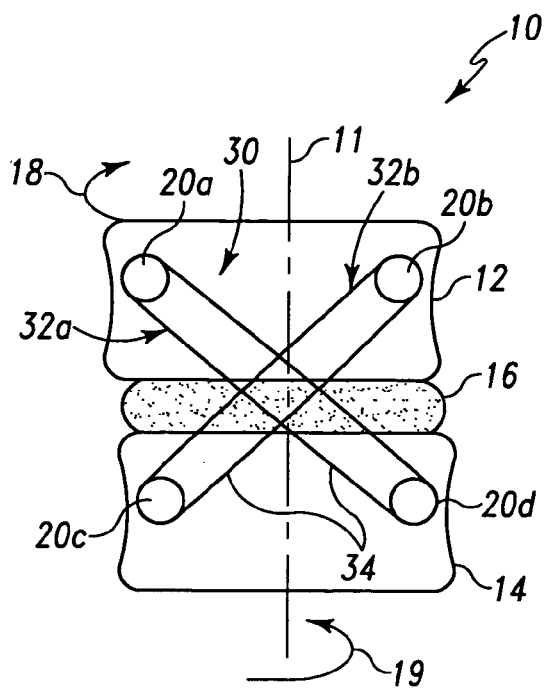
FIG. 2 is a diagrammatic view of a spinal motion segment with one embodiment motion preserving spinal stabilization system engaged thereto.

Referring now to FIG. 2, there is shown one embodiment multi-directional stabilization system 30 secured to spinal column segment 10. System 30 includes first and second trans-axial stabilization constructs 32a, 32b. Each trans-axial construct 32a, 32b extends trans-axially to axis 11 and is engaged to each of the vertebrae 12, 14 at opposite sides of the axis 11. Other embodiments contemplate systems employing one construct or more than two constructs. Constructs 32a and 32b are collectively and individually referred to as construct 32 herein.

Each construct 32 is adapted to extend along at least one vertebral level and between anchors in a trans-axial and oblique orientation to central axis 11 of the spinal column. In FIG. 2, construct 32a extends between anchors 20a and 20d, and construct 32b extends between anchors 20b and 20c. Each construct 32 includes an elongated body 34 that is looped around the receiving portion 22 of the respective anchors 20. Body 34 may be of any suitable form, such as a tether, suture, wire, tether, band, cord, cable, or rope, for example. Body 34 may also be made from any material compatible with the human body, including ceramics, plastics, metals, elastomers, shape memory material, or carbon fiber composites. The opposite ends of body 34 may overlap one another and be secured to one another to form a loop configuration with a crimp, swage, suture, fastener, adhesive, or other suitable means. In another embodiment, body 34 is provided in the form of a continuous loop without overlapping ends.

When looped around anchors 20 as shown in FIG. 2, constructs 32 constrain movement of at least the adjacent sides of vertebrae 12, 14 away from one another by tensioning. Movement of the vertebrae relative to one another by axial rotation is also constrained by the respective construct 32 extending in the direction from the lower vertebra 14 to the upper vertebra 12 that corresponds to the direction of rotation. For example, axial rotation in the direction of arrows 18, 19 is resisted by tensioning of construct 32a.

Figure 3:
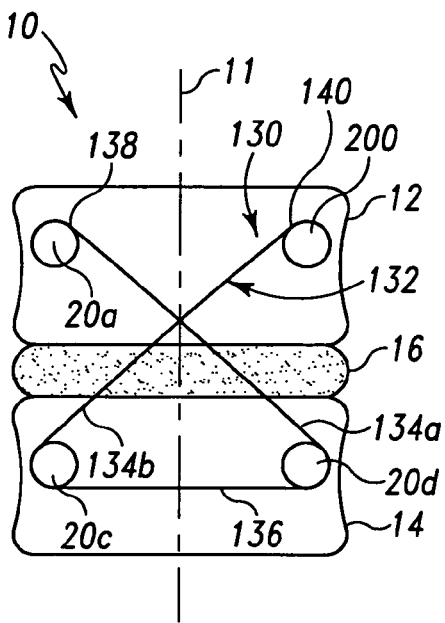
FIG. 3 is a diagrammatic view of the spinal motion segment with another embodiment motion preserving spinal stabilization system engaged thereto.
Figure 4:
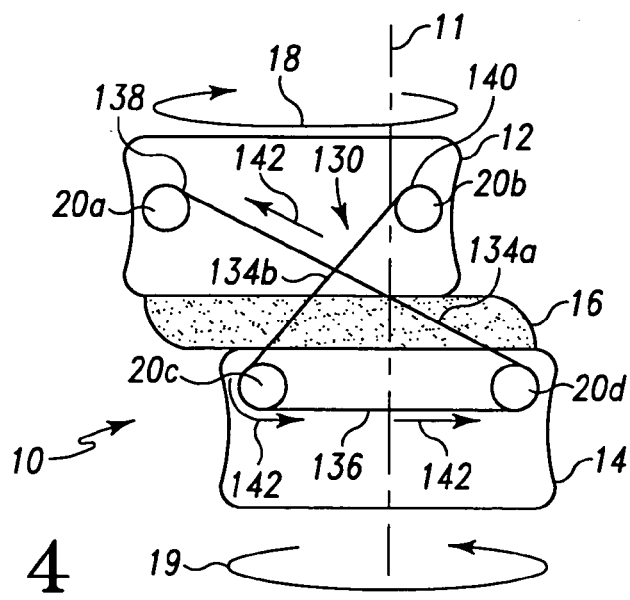
FIG. 4 is a diagrammatic view of the spinal motion segment and system of FIG. 3 with the vertebrae of the motion segment displaced relative to one another to indicate axial rotation of the motion segment.

Referring now to FIG. 3, there is shown another embodiment multi-directional stabilization system 130 secured to spinal column segment 10 with anchors 20. System 130 includes a trans-axial stabilization construct 132 having a body 134 with first and second trans-axial portions 134a, 134b and a connecting portion 136. Each trans-axial portion 134a, 134b extends trans-axially to and is obliquely oriented with central axis 11, and is engaged to each of the vertebrae 12, 14 at opposite sides of the axis 11. Connecting portion 136 extends between anchors 20c and 20d along vertebra 14.

Construct 132 is adapted to extend along at least one vertebral level and between anchors in a trans-axial orientation to central axis 11 of the spinal column. Construct 132 includes an elongated body 134 that is fixedly secured at a first end 138 to anchor 20a and at a second end 140 to anchor 20b. Body 134 extends trans-axially between vertebrae 12, 14 obliquely to axis 11 from anchor 20a to anchor 20d. Body 134 is looped around at least a portion of anchor 20d and extends trans-axially and orthogonally to axis 11 to anchor 20c. Body 134 is further looped around anchor 20c and extends trans-axially between vertebrae 12, 14 from anchor 20c to anchor 20b obliquely to axis 11. A second end 140 of body 134 is fixedly secured to anchor 20b.

Body 134 may be of any suitable form, such as a tether, suture, wire, tether, band, cord, cable, or rope, for example. Ends 138, 140 may be fixedly secured to anchors 20a, 20b by any suitable connection. Ends 138, 140 may be wrapped or looped around the receiving portion 22 of anchor 20. Ends 138, 140 can also be secured in a passage of receiving portion 22 or about a post of receiving portion 22 with a set screw, crimp, spike or other suitable fastening device. Body 134 can be secured to anchors 20c, 20d by positioning body 34 in a groove, recess, receptacle, passage or other structure of receiving portion 22 to allow body 34 to slidably move relative thereto while being retained on receiving portion 22.

Construct 132 is flexible yet tensions to limit or constrain movement of vertebrae 12, 14 away from one another at the respective adjacent side of the vertebrae 12, 14. Movement of the vertebrae relative to one another by axial rotation, as indicated by arrows 18, 19, is also resisted by tensioning of construct 132. Body 134 can slide around anchors 20c, 20d as indicated by arrows 142 so that the tension of construct 132 is maintained during axial rotation. The dynamic connection of body 134 with anchors 20c, 20d allows the length of trans-axial portion 134a between anchors 20a, 20d to increase and the length of trans-axial portion 134b between anchors 20b, 20c to decrease. Axial rotation in the opposite direction would in turn result in sliding movement of body 134 about anchors 20c, 20d in a direction opposite arrows 142, allowing the length of trans-axial portion 134a between anchors 20a, 20d to decrease and the length of trans-axial portion 134b between anchors 20b, 20c to increase. The ability to slide to vary the length between anchors maintains construct 132 in tension between anchors 20.

Figure 5:
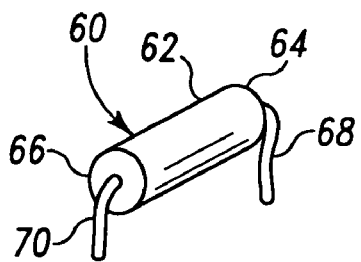
FIG. 5 is a perspective view of another embodiment stabilization construct usable with motion preserving spinal stabilization systems.

Referring now to FIG. 5, there is shown a compression member 60. Compression member 60 includes a body 62 extending between a first end 64 and a second end 66. A first engaging member 68 extends from first end 64 and a second engaging member 70 extends from second end 66. Body 62 can be enlarged relative to engaging members 68. 70 so that ends 64, 66 can be positioned in abutting contact with receiving portions 22 of the respective anchors 20 of differing ones of the vertebrae 12, 14 to limit movement of anchors 20 and thus the vertebrae 12, 14 toward one another. Engaging members 68, 70 can be engaged to the respective adjacent anchor 20 to retain compression member 60 in position relative to the anchors 22.

Figure 6:
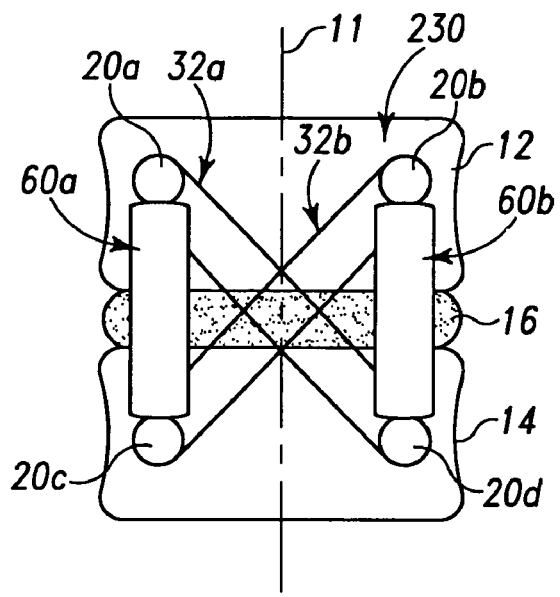
FIG. 6 is a diagrammatic view of the spinal motion segment with another embodiment motion preserving spinal stabilization system including the stabilization construct of FIG. 5 extending axially between anchors engaged to the vertebrae and the trans-axial constructs of FIG. 2 extending trans-axially between the anchors.

One example of a stabilization system 230 is shown in FIG. 6. Stabilization system 230 utilizes trans-axial stabilization constructs 32a, 32b in the manner discussed above. A first compression member 60a is positioned between anchors 20a, 20c with the ends of body 62 in abutting engagement with or positioned adjacent to the receiver portions of the anchors. Engaging member 68 can be engaged to anchor 20a, and engaging member 70 can be engaged to anchor 20c to maintain compression member 60a in engagement with anchors 20a, 20c. Compression member 60b can be similarly engaged between anchors 20b, 20d.

In one form, engaging members 68, 70 are flexible members that permit movement of the vertebrae 12, 14 away from one another and tension to limit such movement. Engaging members 68, 70 can comprise opposite ends of a flexible cord, tether, rope, wire, suture or other member positioned through a passage of body 62. Body 62 may alternatively be overmolded about engaging members 68, 70 to provide an integral structure. Engaging members 68, 70 may be engaged to anchors 20 by any suitable connection. For example, engaging members 68, 70 may be wrapped or looped around the receiving portion 22 of anchor 20. Engaging members 68, 70 can also be secured in a passage of receiving portion 22 or about a post of receiving portion 22 with a set screw, crimp, spike or other suitable fastening device.

Compression member 60a, 60b contact the respective anchors 20 in response to movement of the vertebrae toward one another at the side of the spinal column segment to which system 230 is engaged. Compression members 60a, 60b can also maintain a distraction force between vertebrae 12, 14 by normally exerting outwardly directed forces to the respective anchors 20. Movement of the vertebrae 12, 14 away from one another on the side thereof adjacent system 230 can be limited with constructs 32a, 32b and supplemented by engagement of engaging members 68, 70 with the respective anchors.

Figure 7:
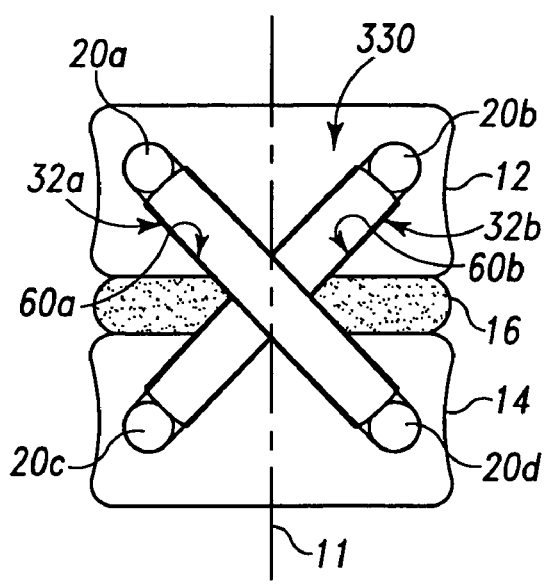
FIG. 7 is a diagrammatic view of the spinal motion segment with another embodiment motion preserving system including the stabilization constructs of FIG. 5 and the stabilization constructs of FIG. 2 extending trans-axially between anchors engaged to the vertebrae.

Another example of a stabilization system 330 is shown in FIG. 7. Stabilization system 330 utilizes trans-axial stabilization constructs 32a, 32b in the manner discussed above. However, compression members 60a, 60b are also positioned trans-axially and obliquely oriented to central axis 11. First compression member 60a is positioned between anchors 20a, 20d with the ends of body 62 in abutting engagement with or positioned adjacent to the receiver portions of the anchors. Engaging member 68 can be engaged to anchor 20a, and engaging member 70 can be engage to anchor 20d to maintain compression member 60a in engagement with anchors 20a, 20d. Compression member 60b can be similarly engaged between anchors 20b, 20c.

Compression members 60a, 60b are positioned within the looped portion of the respective constructs 32a, 32b. Compression members 60a, 60b can be flexed around one another at the location where they cross one another. In another embodiment, the compression members can be notched at the crossing location to minimize the profile of the construct. In still another embodiment, compression members 60a, 60b are integrally formed with one another.

Compression members 60a, 60b contact the respective anchors 20 in response to movement of the vertebrae toward one another or rotating relative to one another at the side of the spinal column segment to which system 330 is engaged. Compression members 60a, 60b can also maintain a distraction force between vertebrae 12, 14 by normally exerting outwardly directed forces to the respective anchors 20.

Figure 8:
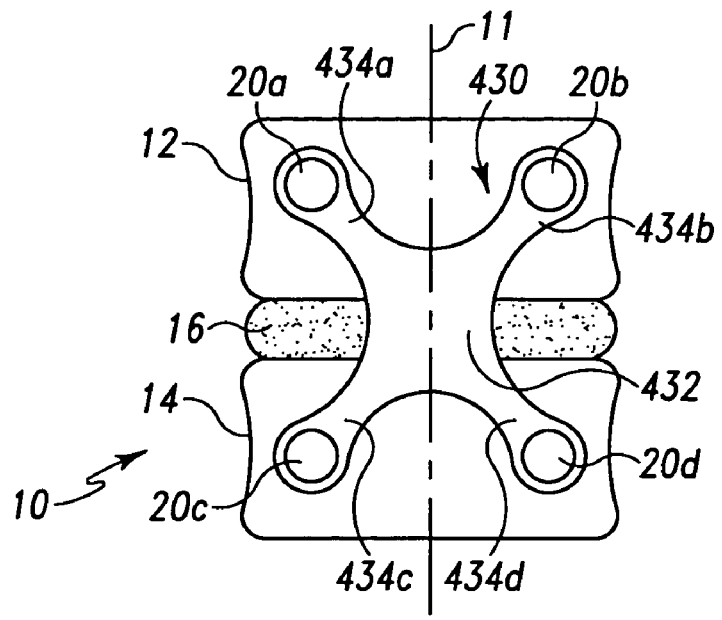
FIG. 8 is a diagrammatic view of the spinal motion segment with another embodiment motion preserving spinal stabilization system engaged thereto.

Referring now to FIG. 8, another embodiment stabilization system includes a construct 430 engaged between vertebrae 12, 14 of spinal column segment 10. Stabilization construct 430 includes an overall X shape including portions extending obliquely to central axis 11 between anchors 20. Construct 430 includes a central body 432 positionable along axis 11 between anchors 20a, 20b, 20c, and 20d. Construct 430 include outwardly extending arms 434a, 434b, 434c, 434d extending from body 432 to respective ones of the anchors 20a, 20b, 20c, 20d.

Construct 430 can be made from a flexible, compressible material that allows movement of vertebrae 12, 14 relative to one another while constraining distraction, compression and axial rotation of vertebrae 12, 14. Arms 434 can be elastic to return toward a non-tensioned or non-compressed state to limit the relative motion of vertebrae 12, 14. Arms 434 can further independently bend or flex relative to body 432 to permit spinal motion. Arms 434 can include holes at the outer ends thereof that allow the arms to be positioned about the respective anchor 20. In another form, the anchors 20 can be positioned through the holes in the arms to secure the arms to the respective vertebrae.

Figure 9:
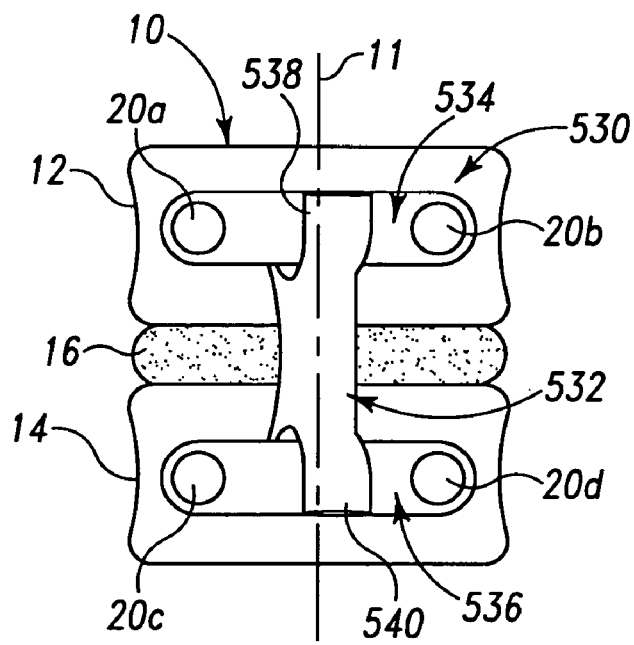
FIG. 9 is a diagrammatic view of the spinal motion segment with another embodiment motion preserving spinal stabilization system engaged thereto.

Referring now to FIG. 9, there is shown another embodiment stabilization system 530 engaged between vertebrae 12, 14 of spinal column segment 10. Stabilization system 530 includes an overall shape that forms an "I" type configuration with a central construct and transversely extending upper and lower constructs. The upper and lower constructs can be engaged bi-laterally to the respective vertebra 12, 14, and the central construct is positioned centrally between the lateral ends of the upper and lower constructs.

In the illustrated embodiment of FIG. 9, the upper and lower constructs 534, 536 include members that extend transversely to central axis 11 between anchors 20a, 20b engaged to vertebra 12 and anchors 20c, 20d engaged to vertebra 14, respectively. Central construct 532 includes a member that extends between the upper and lower constructs 534, 536. Central construct 532 can be positionable to extend along or in the generally direction of central axis 11 between an intermediate portion of upper construct 534 and an intermediate portion of lower construct 536.

The constructs 532, 534, 536 may be formed from one component or multiple components. Constructs 532, 534, 536 can be made from a flexible, compressible material that allows movement of vertebrae 12, 14 relative to one another while constraining distraction, compression and axial rotation of vertebrae 12, 14. In one embodiment, central body 532 is rigid and at least one of the upper and lower constructs 534, 536 can be flexible and elastic to return toward a non-tensioned or non-compressed state to allow yet limit the relative motion between vertebrae 12, 14. Other embodiments contemplate that the other of the upper and lower constructs 534, 536 is rigid, or that the other of the upper and lower constructs 534, 536 is flexible. The flexible upper and/or lower constructs 534, 536 can independently bend or flex relative to central construct 532 to permit spinal motion. Connection of constructs 534, 536 with central construct 532 can resist torsional movement and compression of the vertebrae.

Constructs 534, 536 can be in the form of a rod, bar, linkage, plate, or other elongate member and include holes at the outer laterally oriented ends thereof that allow positioning about the respective anchor 20. In another form, the anchors 20 can be positioned through holes in the construct to secure the constructs to the respective vertebrae. It is also contemplated that the lateral ends can be received in an anchor and secured therein with a set screw, cap or other device. In still another form, constructs 534, 536 include engaging members extending therefrom such as discussed above with respect to compression member 60 that are engaged to the anchors 20 by looping or wrapping about the anchors, or that extend into and are secured in a passage of the anchor.

In another embodiment, upper and lower constructs 534, 536 can be rigid and central construct 532 is flexible to permit at least limited movement of vertebrae 12, 14 toward one another while exerting return forces toward a non-tensioned or non-compressed state to limit the relative motion between vertebrae 12, 14. Central construct 532 can be in the form of a rod, bar, plate, linkage or other elongate member and include opposite ends 538, 540 adapted to engage a respective one of the upper and lower constructs 534, 536. In the illustrated embodiment, the ends include a U-shaped receptacle to receive the respective upper and lower constructs 534, 536. In other embodiments, the ends can engage the respective upper and lower constructs 534, 536 to limit movement of vertebrae 12, 14 away from one another. Such engagement can include providing the ends of central construct 532 with any one or combination of an I-bolt configuration, a hook, a clamp, a set screw, a reduced size received in a bore of the upper and lower constructs 534, 536, or a friction fit, for example. In another embodiment, the ends of central construct 532 can include an engaging member such as a tether or cord that is wrapped around or received and secured in the respective adjacent upper and lower constructs 534, 536.

The stabilization constructs can be made from one or more materials that possess the appropriate strength characteristics necessary to withstand loading from the human body and, depending on its function, allow compression or distraction of the adjacent vertebrae while constraining relative motion therebetween. The constructs can be made from materials including ceramics, plastics, metals, elastomers, shape memory materials, or carbon fiber composites. The constructs are obliquely oriented to the central axis of the spinal column and form an X-shape extending between anchors of the adjacent vertebrae, providing effective constraint of axial rotation and distraction of the adjacent vertebrae while preserving the motion capabilities of the spinal motion segment.

The above described alternative configurations for the constructs can have dimensions that will vary depending upon the specific design necessary for a specific patient. More particularly, the dimensions and geometric shapes can vary based on patient anatomy, physiology, and the type of material or materials used in the construct. Specific applications are contemplated in posterior stabilization procedures where anchors are engaged to pedicles of the vertebrae and the stabilization constructs are engaged to the anchors.

While the invention has been illustrated and described in detail in the drawings and foregoing description, the same is to be considered as illustrative and not restrictive in character. All changes and modifications that come within the spirit of the invention are desired to be protected.

What is claimed is:

1. A multi-directional spinal stabilization system, comprising:
    a first anchor engageable to a first vertebra on a first side of a central axis of a spinal column and a second anchor engageable to the first vertebra on a second side of the central axis;
    a third anchor engageable to a second vertebra on the first side of the central axis and a fourth anchor engageable to the second vertebra on the second side of the central axis;
    a first stabilization construct including an elongate flexible body in the form of a loop positionable about the first and fourth anchors and a first compression member positioned between said first and fourth anchors when said first and fourth anchors are engaged on said first and second sides of the central axis, respectively, wherein said loop resists movement of said first and fourth anchors away from one another and said compression member resists movement said first and fourth anchors toward one another; and
    a second stabilization construct including an elongate flexible body in the form of a loop positionable about the second and third anchors and a second compression member positioned between said second and third anchors when said second and third anchors are engaged on said first and second sides of the central axis, respectively, wherein said loop resists movement of said second and third anchors away from one another and said compression member resists movement said second and third anchors toward one another, wherein when engaged to said respective anchors said second stabilization construct extends transversely to said first stabilization construct and each of said first and second stabilization constructs are obliquely oriented to the central axis.

2. The system of claim 1, wherein said anchors each include a distal engaging portion threadingly engageable with the respective vertebrae and a proximal receiving portion engageable with the respective construct.

3. The system of claim 1, further comprising:
said first compression member including a compressible body positionable between the first and fourth anchors with said compressible body providing distraction between the first and fourth anchors when compressed; and
said second compression member including a compressible body positionable between the second and third anchors with said compressible body providing distraction between the second and third anchors when compressed, wherein when positioned between said respective anchors said second compression member extends transversely to said first compression member and each of said first and second compression members are obliquely oriented to the central axis.

4. The system of claim 3, wherein:
said first compression member includes a first end positionable in contact with the first anchor and an opposite second end positionable in contact with the fourth anchor, said first compression member further including engaging members extending from each of said first and second ends for engagement with an adjacent one of said first and fourth anchors; and
said second compression member includes a first end positionable in contact with the second anchor and an opposite second end positionable in contact with the third anchor, said second compression member further including engaging members extending from each of said first and second ends for engagement with an adjacent of said second and third anchors.

5. The system of claim 4, wherein said engaging members are flexible.

6. A multi-directional spinal stabilization system, comprising:
a first anchor engageable to a first vertebra on a first side of a central axis of a spinal column and a second anchor engageable to the first vertebra on a second side of the central axis;
a third anchor engageable to a second vertebra on the first side of the central axis and a fourth anchor engageable to the second vertebra on the second side of the central axis; and
a stabilization construct including an elongate flexible body having a first trans-axial portion engageable to the first anchor and extendable obliquely across the central axis to the fourth anchor, a second trans-axial portion engageable to the second anchor and extendable obliquely across the central axis to the third anchor, and a connecting portion extendable across the central axis between the third and fourth anchors, wherein said stabilization construct is slidable relative to the third and fourth anchors when said third and fourth anchors are engaged to the second vertebra in response to axial rotation of the first and second vertebrae to maintain tension on the stabilization construct.

7. The system of claim 6, wherein said third and fourth anchors each include a proximal receiving portion and said stabilization construct is positionable about and slidably received relative to said proximal receiving portions.

8. The system of claim 6, wherein said stabilization construct is fixedly engaged to said first and second anchors.

9. A multi-directional spinal stabilization system, comprising:
a first anchor engageable to a first vertebra on a first side of a central axis of a spinal column and a second anchor engageable to the first vertebra on a second side of the central axis;
a third anchor engageable to a second vertebra on the first side of the central axis and a fourth anchor engageable to the second vertebra on the second side of the central axis; and
a first member structured for positioning between and engagement to said first and second anchors and a second member structured for positioning between and engagement to said third and fourth anchors; and
a third member engageable to said first member between said first and second anchors and structured to extend from said first member to said second member, said third member further being engageable to said second member between said third and fourth anchors, wherein at least one of said first, second and third members is flexible and at least one other of said first, second and third members is rigid.

10. The system of claim 9, wherein said third member is positionable to extend along the central axis when engaged to the first and second members.

11. The system of claim 9, wherein said third member is flexible and said first and second members are rigid.

12. The system of claim 9, wherein said first member is flexible and said third member is rigid.

13. The system of claim 12, wherein said second member is flexible.

14. The system of claim 9, wherein said third member includes opposite ends each defining a receptacle for receiving a respective one of said first and second members.

15. A method for stabilizing at least one level of a spinal column segment, comprising:
engaging a first anchor to a first vertebra on a first side of a central axis of the spinal column;
engaging a second anchor to the first vertebra on a second side of the central axis;
engaging a third anchor to a second vertebra on the first side of the central axis;
engaging a fourth anchor to the second vertebra on the second side of the central axis;
positioning a first elongate stabilization construct about the first anchor and the fourth anchor in an oblique orientation to the central axis;
positioning a second elongate stabilization construct about the second anchor and the third anchor in an oblique orientation to the central axis, wherein the first and second stabilization constructs each form a loop extending between the respective anchors to which each is engaged;
positioning a first compression member including a compressible body between the first and fourth anchors; and
positioning a second compression member including a compressible body between the second and third anchors, wherein when positioned between the respective anchors the second compression member extends transversely to the first compression member and each of the first and second compression members are obliquely oriented to the central axis, said first and second compression members being elastic to provide distraction when compressed between respective ones of the first and fourth anchors and the second and third anchors.

16. The method of claim 15, wherein the first compression member is positioned within the loop of the first stabilization construct and the second compression member is positioned within the loop of the second stabilization construct.

17. A method for stabilizing a spinal motion segment, comprising:

engaging a first anchor to a first vertebra on a first side of a central axis of the spinal column;

engaging a second anchor to the first vertebra on a second side of the central axis;

engaging a third anchor to a second vertebra on the first side of the central axis;

engaging a fourth anchor to the second vertebra on the second side of the central axis;

fixing a first end of an elongated, flexible stabilization construct to the first anchor;

extending the stabilization construct from the first anchor trans-axially and obliquely to the central axis to the fourth anchor;

securing the stabilization construct to the fourth anchor;

extending stabilization construct trans-axially from the fourth anchor to the third anchor;

securing the stabilization construct to the third anchor;

extending the stabilization construct from the third anchor trans-axially to and obliquely to the central axis to the second anchor; and fixing a second end of the stabilization construct to the second anchor, wherein the stabilization construct is slidable relative to the third and fourth anchors in response to axial rotation of the spinal column segment.

18. The method of claim 17, wherein each anchor is engaged to a respective pedicle of the first and second vertebrae.

19. The method of claim 17, wherein a length of the stabilization construct between the first and fourth anchors and a length of the stabilization construct between the second and third anchors vary in response to axial rotation of the spinal column segment and sliding movement of the stabilization construct relative to the third and fourth anchors.

* * * * *